(12) United States Patent
Biedebach et al.

(10) Patent No.: US 9,707,112 B2
(45) Date of Patent: Jul. 18, 2017

(54) CONCENTRIC CATHETER FOR POSITIONING A POLYMERIC URETHRAL STENT IMPLEMENTING RESISTANCE HEATING

(71) Applicants: Mark Conrad Biedebach, Long Beach, CA (US); Raymond A. Sleiman, Long Beach, CA (US)

(72) Inventors: Mark Conrad Biedebach, Long Beach, CA (US); Raymond A. Sleiman, Long Beach, CA (US)

( * ) Notice: Subject to any disclaimer, the term of this patent is extended or adjusted under 35 U.S.C. 154(b) by 23 days.

(21) Appl. No.: 14/849,062

(22) Filed: Sep. 9, 2015

(65) Prior Publication Data

US 2016/0067072 A1 Mar. 10, 2016

Related U.S. Application Data

(60) Provisional application No. 62/047,873, filed on Sep. 9, 2014.

(51) Int. Cl.
*A61F 2/95* (2013.01)
*A61F 2/04* (2013.01)
*A61F 2/958* (2013.01)
*A61F 2/945* (2013.01)

(52) U.S. Cl.
CPC ............... *A61F 2/95* (2013.01); *A61F 2/945* (2013.01); *A61F 2/958* (2013.01); *A61F 2002/047* (2013.01)

(58) Field of Classification Search
None
See application file for complete search history.

(56) References Cited

U.S. PATENT DOCUMENTS

| 5,312,430 A * | 5/1994 | Rosenbluth | A61F 2/958 600/105 |
| 5,957,974 A * | 9/1999 | Thompson | A61F 2/07 623/1.11 |
| 2003/0163190 A1* | 8/2003 | LaFont | A61B 18/1492 623/1.11 |
| 2009/0149946 A1* | 6/2009 | Dixon | A61F 2/07 623/1.36 |
| 2013/0261729 A1* | 10/2013 | Gillick | A61F 2/958 623/1.12 |

* cited by examiner

*Primary Examiner* — Thomas J Sweet
*Assistant Examiner* — Wade P Schutte

(57) ABSTRACT

A concentric tube catheter for positioning a polymeric urethral stent implementing resistance heating to make the stent malleable for insertion into a urinary tract. An inflatable bladder is mounted to one end of the concentric tube catheter with the stent positioned around the inflatable bladder. The concentric tube catheter charged with a quantity of fluid. A static pressure control assembly and a variable pressure control assembly are in fluid connection with the concentric tube catheter. The quantity of fluid is pressurized within the concentric tube catheter with the static pressure control assembly in order to expand the inflatable bladder. A heating control system is used to increase the temperature of the stent allowing to become more malleable. The variable pressure control assembly oscillates the quantity of fluid to distribute heat evenly to the inflatable bladder and therefore to the stent. As the inflatable bladder expands, the malleable stent also expands.

9 Claims, 6 Drawing Sheets

CONCENTRIC CATHETER FOR POSITIONING A POLYMERIC URETHRAL STENT IMPLEMENTING RESISTANCE HEATING

The current application claims a priority to the U.S. Provisional Patent application Ser. No. 62/047,873 filed on Sep. 9, 2014.

FIELD OF THE INVENTION

The present invention relates generally to a catheter. More specifically, the present invention relates to a catheter implementing resistance heating and a polymeric urethral stent for the alleviation of pathologically constricted flow through the lumen of the urethra.

BACKGROUND OF THE INVENTION

A stent is a tissue support device that is inserted in order to open (and keep open) the lumen of a vessel, duct, tract, or tube within the body. It can be used to treat a condition whereby the lumen of a vessel becomes constricted (stenosis). In the urinary system, an example of stenosis is benign prostatic hyperplasia (BPH).

Conventional urethral stents exist in two major categories or types: self-expanding, and balloon-expanding. The latter type of stent can be positioned over the balloon end of a balloon catheter. The catheter-stent assembly can then be inserted into the lumen of the urethra, and then guided to a target site where it can remain implanted for months (or years). At the present time, the only available urethral stents are of the expanding metal type, and have yet to prove themselves for long term implant use. There is, therefore, considerable need for a non-metallic balloon-expandable urethral stent.

In order to prevent migration of the stent from its intended location in the vessel, the stent will contain an array of small plastic protrusions that emerge only upon expansion. However, endothelial tissue may grow into the outer surface of the stent and help to keep it in place.

If removal of the stent becomes necessary, it should be possible with minimal pain and/or discomfort, minimal risk of tissue insult or damage, and minimal procedural complexity.

DETAIL DESCRIPTIONS OF THE INVENTION

All illustrations of the drawings are for the purpose of describing selected versions of the present invention and are not intended to limit the scope of the present invention.

The present invention is a concentric catheter for positioning a polymeric urethral stent implementing resistance heating. The present invention allows for the insertion of a urethral stent within a person's body in order to open and keep open the lumen of a urinary tract. The urinary tract can become restricted through various medical conditions, such as benign prostatic hyperplasia. Opening of the urinary tract allows urine to be excreted from the person properly helping to avoid complications of such medical conditions.

Figure 1:
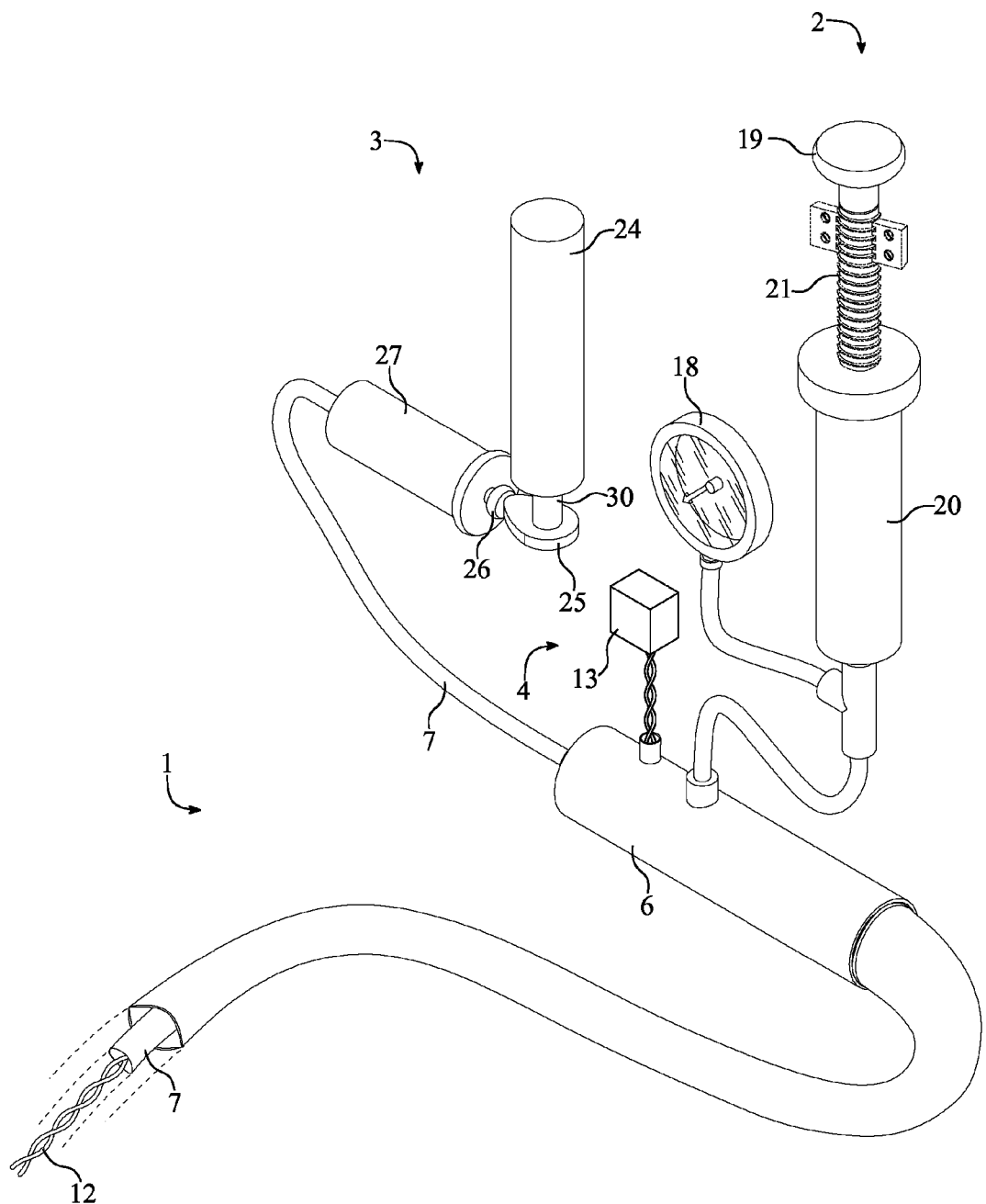
FIG. 1 is a perspective view of the static pressure control assembly, the variable pressure control assembly, the heating control assembly, the open end of the inner concentric tube catheter, and the closed end of the outer concentric tube catheter.
Figure 2:
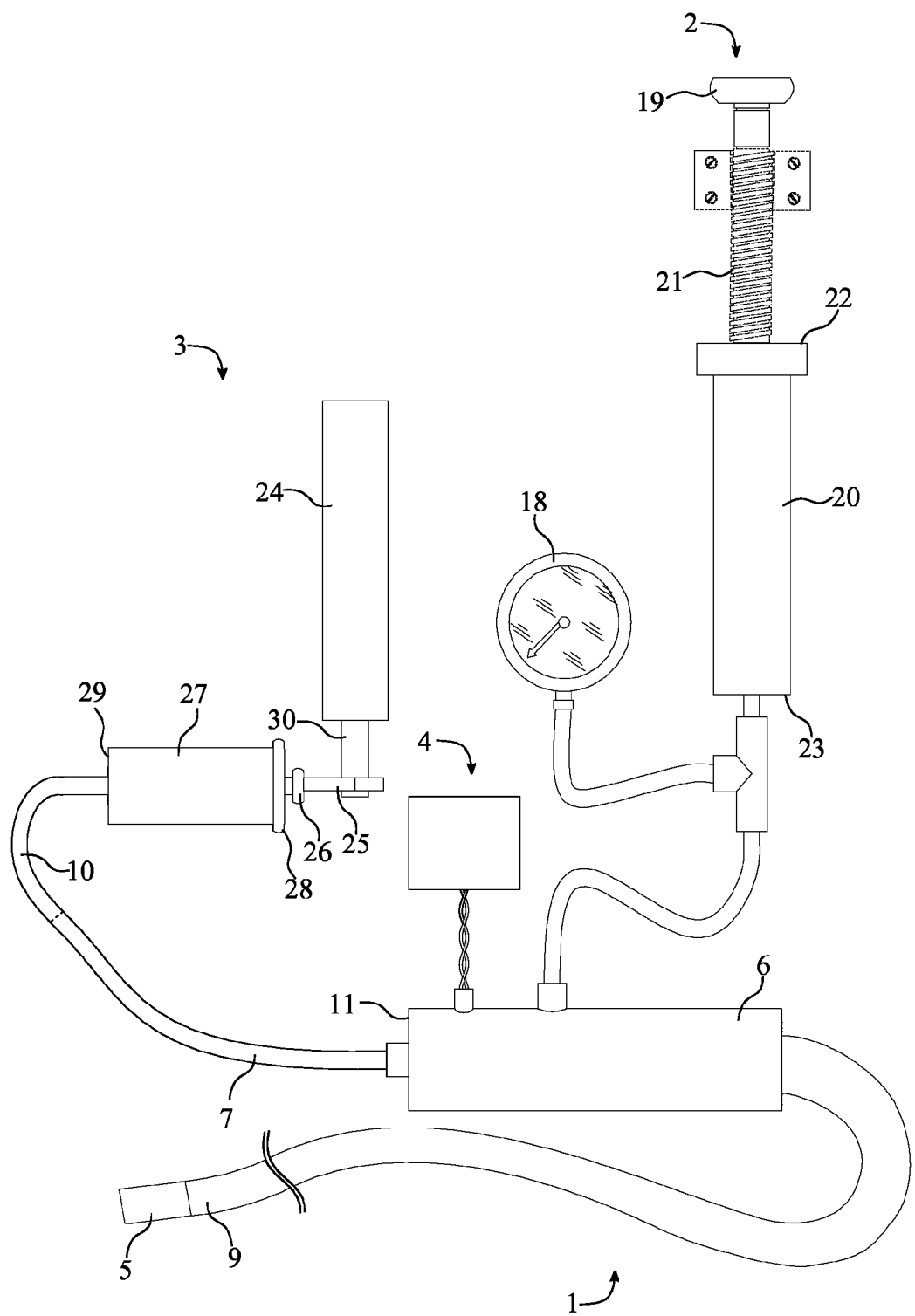
FIG. 2 is a front view of the static pressure control assembly, the variable pressure control assembly, the heating control assembly, the open end of the inner concentric tube catheter, and the closed end of the outer concentric tube catheter.

As shown in FIG. 1 and FIG. 2, the present invention comprises a concentric tube catheter 1, a static pressure control assembly 2, a variable pressure control assembly 3, and a heating control assembly 4. The concentric tube catheter 1 is a vessel which contains a quantity of fluid and allows the positioning of a stent within a patient's urinary tract. The static pressure control assembly 2 allows for a controlled increase in pressure within the concentric tube catheter 1, while the variable control assembly 3 oscillates a flow of the quantity of fluid within the concentric tube catheter 1. The concentric tube catheter 1 comprises an outer catheter tube 6, an inner catheter tube 7, and an inflatable bladder 8. The quantity of fluid is used to increase the pressure within the concentric tube catheter 1 in order to evenly expand the inflatable bladder 8. The quantity of fluid is contained within a volume defined by concentric catheter tube 1, the static pressure control assembly 2, and the variable pressure control assembly 3.

Figure 3:
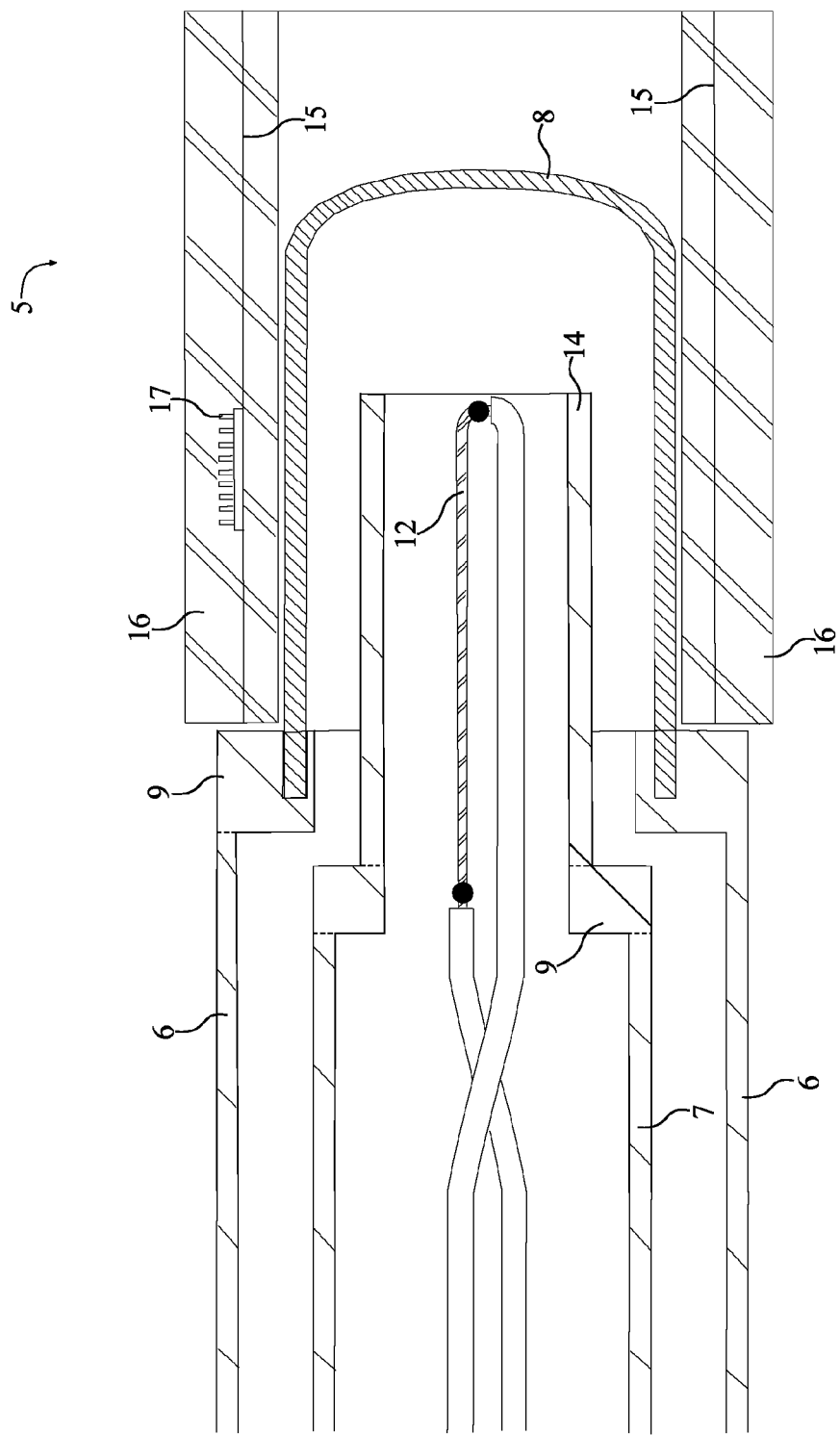
FIG. 3 is a cross-sectional view of the insertion end for both the inner catheter tube and the outer catheter tube, the heating wire, the inflatable bladder, and the stent.

The outer catheter tube 6 and the inner catheter tube 7 each comprise an insertion end 9 as shown in FIG. 3. The insertion end 9 is the portion of the concentric tube catheter 1 which is guided into the patient. An open end 10 of the inner catheter tube 7, which is opposite to the insertion end 9 of the inner catheter tube 7, which is opposite to the insertion end 9 of the outer catheter tube 6, traverses through a closed end 11 of the outer catheter tube 6 and the inner catheter tube 7 is mounted concentrically within the outer catheter tube 6, as shown in FIG. 1 and FIG. 2. This configuration allows static pressure control assembly 2 to be in fluid communication with the outer catheter tube 6, adjacent to the closed end 11 of the outer catheter tube 6, and the variable pressure controller to be in fluid communication with the open end 10 of the inner catheter tube 7. In accordance to FIG. 3, the inflatable bladder 8 is mounted on the insertion end 9 of the outer catheter 6 such that the inflatable bladder 8 extends out from the insertion end 9 of the outer catheter 6 as the pressure increases.

Figure 4:
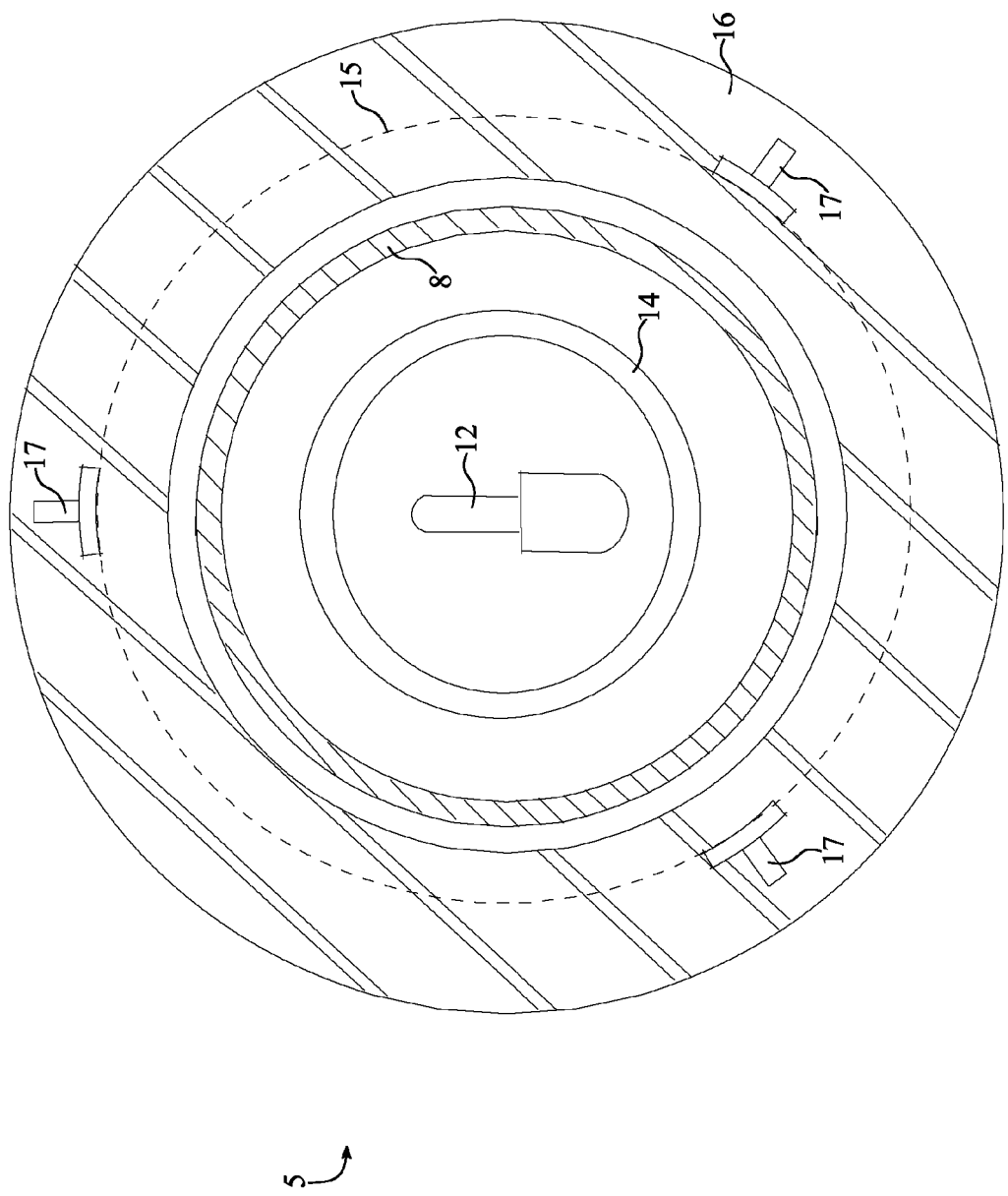
FIG. 4 is cross-sectional view normal to the insertion end for each the inner catheter tube and the outer catheter tube of the present invention.

In accordance to the preferred embodiment, the present invention comprises a stent 5, which the catheter positions within the lumen of the urinary tract. The heating control assembly 4 increases the temperature of the quantity of fluid such that heat is transferred through the inflatable bladder 8 and to the stent 5. Heating the stent 5 causes the stent 5 to become malleable, such that the stent 5 is able to expand radially to open the urinary tract. In order to heat the stent 5, the heating control assembly 4 comprises a heating wire 12 and a current controller 13. The heating wire 12 provides resistance heating as a current from the current controller 13 is flowing through the heating wire 12. The current controller 13 is electrically connected to the heating wire 12 in order to produce a direct electrical current signal to pass through the heating wire 12. As the current flows through the heating wire 12, the heating wire 12 increases surface temperature which is transferred through the quantity of fluid, the inflatable bladder 8, and finally to the stent 5. The heating wire 12 is concentrically positioned within the inner catheter tube 7 such that the heating wire 12 is in direct contact with the quantity of fluid for conductive heat transfer. In accordance to the preferred embodiment, the present invention further comprises an insulation tube 14, as shown in FIG. 3 and FIG. 4. The insulation tube 14 is mounted onto the insertion end 9 of the inner catheter tube 7 and positioned about the heating wire 12. The heating wire 12 is surrounded by the insulation tube 14 to prevent direct contact from the heating wire 12 with other components of the present invention, such as the inflatable bladder 8. The insulation tube 14 is preferred to be polytetrafluoroethylene, or more commonly known as Teflon; however the insulation tube 14 may be made from another suitable electrically insulating material. The heating wire 12 is capable of dissipating one to two watts of heat in order to raise the temperature of the stent 5 to the required temperature for malleability, approximately 43 degrees Celsius to 51 degrees Celsius.

Figure 5:
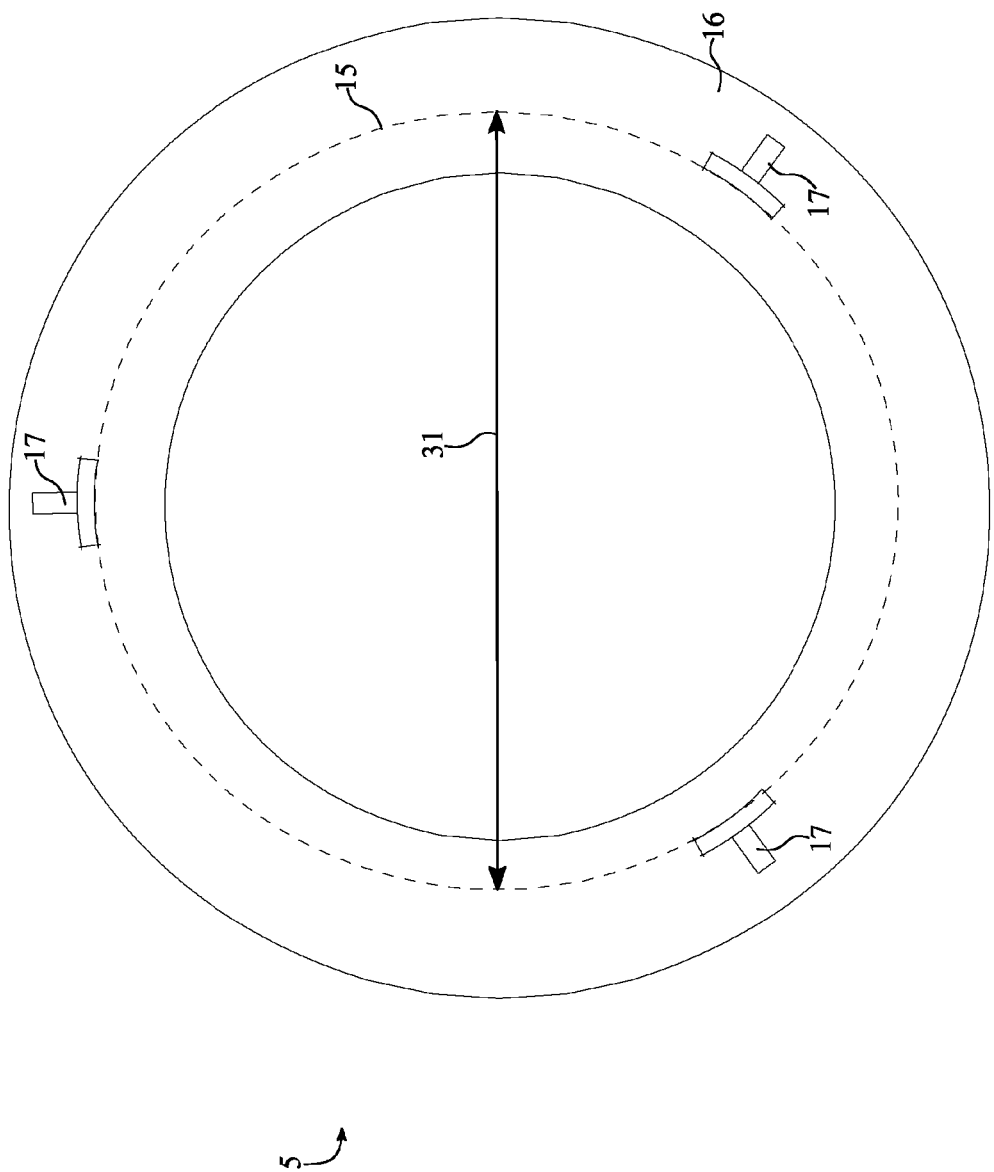
FIG. 5 is a front view of the stent in an unexpanded configuration.
Figure 6:
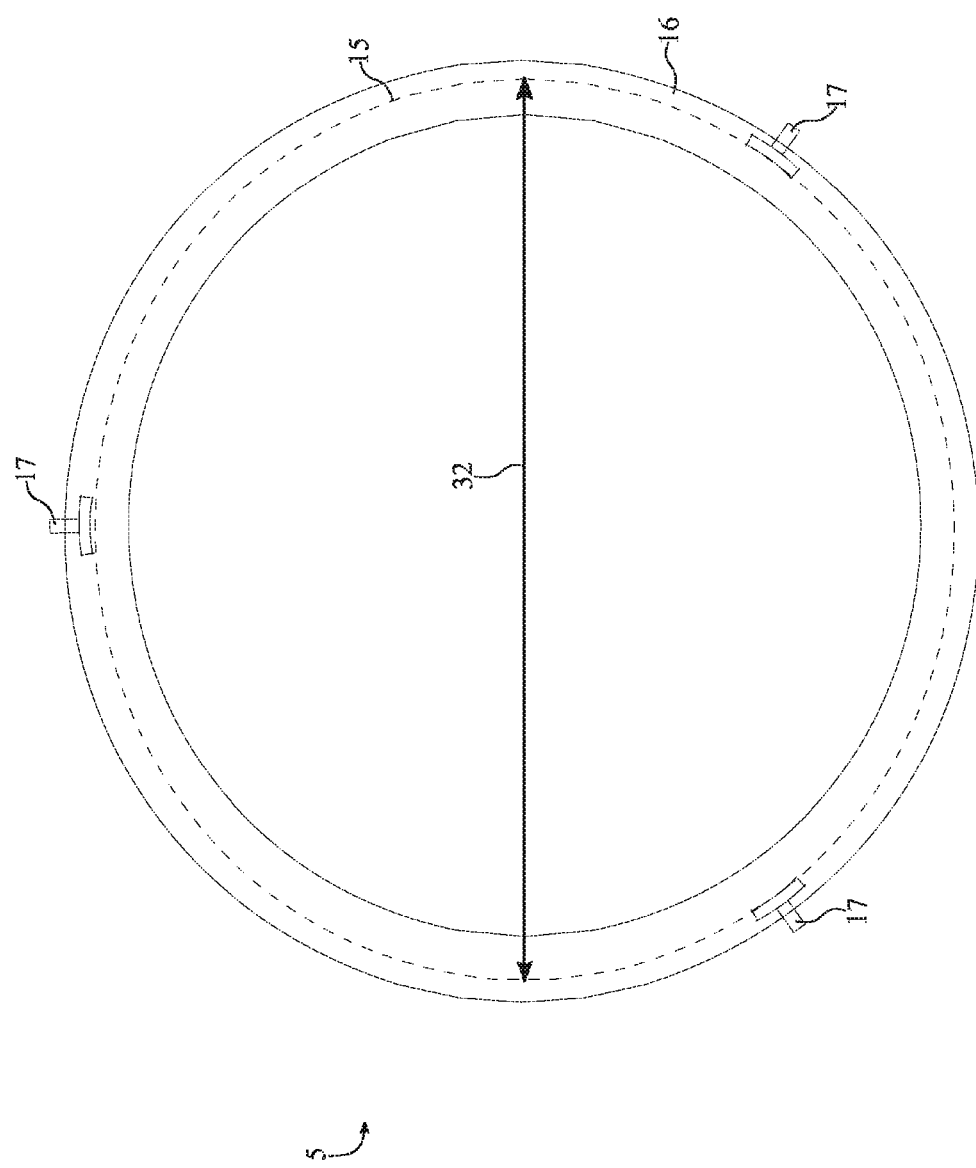
FIG. 6 is a front view of the stent in an expanded configuration.

In accordance to FIG. 4 to FIG. 6, the stent 5 itself is preferred to be comprised of a tubular textile mesh 15, a heat malleable coating 16, and a plurality of protrusions 17. The tubular textile mesh 15 is an elastic hollow cylinder which is enveloped by the heat malleable coating 16. The plurality of protrusions 17 assists in securing the stent 5 in position within the urinary tract such that the stent 5 is less likely to migrate from the intended location. The plurality of protrusions 17 is externally mounted about the tubular textile mesh 15. The heat malleable coating 16 allows the stent 5 to be configured between an unexpanded configuration, the insertion configuration, and an expanded configuration, the operating configuration.

For insertion into the urinary tract, the stent 5 is attached to the insertion end 9 of the outer tubular catheter tube 6 and positioned about the inflatable bladder 8. In order to achieve this, the stent 5 is initially in the unexpanded configuration, wherein the plurality of protrusions 17 are enveloped by the heat malleable coating 16. The insertion end 9 of the inner catheter tube 7 and the heating wire 12 traverse into the stent 5, as shown in FIG. 5. Once guided to the target location of the urinary tract, a direct electrical current signal is emitted through the heating wire 12 to begin heating the stent 5. Simultaneously, the quantity of fluid begins to oscillate within the concentric tube catheter 1, as facilitated by the variable pressure control assembly 3. The oscillation of the quantity of fluid allows for a more uniform transfer of heat to the stent 5. The pressure within the concentric tube catheter 1 is then increased through use of the static pressure control assembly 2 in order to expand the inflatable bladder 8 and therefore apply pressure radially to the stent 5. In some embodiments, the present invention comprises a pressure gauge 18. The pressure gauge 18 displays the pressure within the concentric tube catheter 1, as the pressure gauge 18 is in fluid communication with the concentric tube catheter 1. When the malleable temperature is achieved, the stent 5 will increase in diameter to the expanded configuration, wherein a current diameter 32 of the stent 5 is larger than an initial diameter 31 of the stent 5 in the unexpanded configuration, as shown in FIG. 6. As the stent 5 expands, the external layer of the heat malleable coating 16 on the tubular textile mesh 15 thins. Thus, the plurality of protrusions 17 traverses out of the heat malleable coating 16 to secure the stent 5 within the urinary tract. Once the stent 5 is configured in the expanded configuration, the stent 5 is cooled in order to allow the heat malleable coating 16 to solidify. When the heat malleable coating 16 is solidified, the concentric tube catheter 1 is able to be removed from the patient, while leaving the stent 5 in position within the urinary tract.

In accordance to the preferred embodiment, the static pressure assembly 2 comprises a turn knob 19, a female threaded cylinder 20, and a male threaded piston 21, as shown in FIG. 1 and FIG. 2. The female threaded cylinder 20 comprises a first end 22 and a second end 23. The turn knob 19 is axially connected to the male threaded piston 21 such that the turn knob 19 and the male threaded piston 21 revolve at the same rate when rotated. The male threaded piston 21 sealably engages the female threaded cylinder 20, thus preventing any of the quantity of fluid from escaping. The male threaded piston 21 traverses through the first end 22 of the female threaded cylinder 20. The turn knob 19 extends away from the female threaded cylinder 20 such that it is easily accessible for operation. The second end 23 of the female threaded cylinder 20 is in fluid communication with the outer catheter tubing 6. This configuration for the static pressure assembly 2 allows a user to adjust the pressure within the concentric tube catheter 1 by turning the turn knob 19. As the turn knob 19 is rotated, the male threaded piston 21 slides along the female threaded cylinder 20 either decreases the volume the quantity of fluid is able to occupy, therefore increasing the pressure, or increases the volume the quantity of fluid is able to occupy, therefore decreasing the pressure within the concentric tube catheter 1.

Further in accordance to the preferred embodiment, the variable pressure assembly 3 comprises a motor 24, a cam 25, a piston 26, and a hollow cylinder 27, as shown in FIG. 1 and FIG. 2. The hollow cylinder 27 comprises a first end 28 and a second end 29. The cam 25 is axially mounted to a drive-shaft 30 of the motor 24 and perimetrically pressed against the piston 26. The second end 29 of the hollow cylinder 27 is in fluid communication with the inner catheter tube 7. The piston 26 traverses through the first end 28 of the hollow cylinder 27 and slidably and sealably engages the hollow cylinder 27. This configuration allows the piston 26 to reciprocate within the hollow cylinder 27 to oscillate the fluid flow within the concentric tube catheter 1. As the drive-shaft 30 turns the cam 25, the oval shape of the cam 25 engaging the piston 26 periodically increases and decreases the volume which the quantity of fluid is able to occupy and therefore reciprocating the fluid flow within the concentric tube catheter 1 to disperse the heat evenly to the inflatable bladder 8.

Although the invention has been explained in relation to its preferred embodiment, it is to be understood that many other possible modifications and variations can be made without departing from the spirit and scope of the invention as hereinafter claimed.

What is claimed is:
1. A concentric tube catheter for positioning a polymeric urethral stent implementing resistance heating comprising:
  a concentric tubular catheter;
  a static pressure control assembly;
  a variable pressure control assembly;
  a heating control system;
  the concentric tubular catheter comprising an outer catheter tube, an inner catheter tube and an inflatable bladder;
  the outer catheter tube and the inner catheter tube each comprising an insertion end;

the heating control assembly comprising a heating wire and a current controller;

an open end of the inner catheter tube traversing through a closed end of the outer catheter tube;

the inner catheter tube being mounted concentrically within the outer catheter tube;

the inflatable bladder being mounted on the insertion end of the outer catheter tube;

the static pressure control assembly being in fluid communication with the outer catheter tube, adjacent to the closed end of the outer catheter;

the variable pressure control assembly being in fluid communication with the open end of the inner catheter tube;

the heating wire being concentrically positioned within the inner catheter tube;

the current controller being electrically connected to the heating wire;

the static pressure assembly comprising a turn knob, a female threaded cylinder and a male threaded piston;

the female threaded cylinder comprising a first end and a second end;

the turn knob being axially connected to the male threaded piston;

the male threaded piston sealably engaging the female threaded cylinder;

the male threaded piston traversing through the first end of the female threaded cylinder; and the second end of the female threaded cylinder being in fluid communication with the outer catheter tubing.

2. The concentric tube catheter for positioning a polymeric urethral stent implementing resistance heating, as claimed in claim 1, further comprising:

a stent;

the stent being attached adjacent to the insertion end of the outer catheter tube;

the stent being positioned about the inflatable bladder; and the insertion end of the inner catheter tube and the heating wire traversing into the stent.

3. The concentric tube catheter for positioning a polymeric urethral stent implementing resistance heating, as claimed in claim 2, further comprising:

the stent comprising a tubular textile mesh and a heat malleable coating; and the tubular textile mesh being enveloped by the heat malleable coating.

4. The concentric tube catheter for positioning a polymeric urethral stent implementing resistance heating, as claimed in claim 2, further comprising:

the stent comprising a tubular textile mesh and a plurality of protrusions;

the plurality of protrusions being externally mounted about the tubular textile mesh; and the plurality of protrusions being distributed along the tubular textile mesh.

5. The concentric tube catheter for positioning a polymeric urethral stent implementing resistance heating, as claimed in claim 2, further comprising:

the stent being in an unexpanded configuration;

the stent comprising a tubular textile mesh, a plurality of protrusions and a heat malleable coating;

the plurality of protrusions being externally mounted about the tubular textile mesh; and the tubular textile mesh and the plurality of protrusions being enveloped by the heat malleable coating.

6. The concentric tube catheter for positioning a polymeric urethral stent implementing resistance heating, as claimed in claim 2, further comprising:

the stent being in an expanded configuration, a current diameter of the stent being larger than an initial diameter of the stent in an unexpanded configuration;

the stent comprising a tubular textile mesh, a plurality of protrusions and a heat malleable coating;

the plurality of protrusions being externally mounted about the tubular textile mesh;

the tubular textile mesh being enveloped by the heat malleable coating; and the plurality of protrusions traversing out of the heat malleable coating.

7. The concentric tube catheter for positioning a polymeric urethral stent implementing resistance heating, as claimed in claim 1, further comprising:

a insulation tube; and the insulation tube being mounted onto the insertion end of the inner catheter tube; and the insulation tube being positioned about the heating wire.

8. The concentric tube catheter for position a polymeric urethral stent implementing resistance heating, as claimed in claim 1, further comprising:

a pressure gauge; and the pressure gauge being in fluid communication with the concentric tubular catheter.

9. The concentric tube catheter for positioning a polymeric urethral stent implementing resistance heating, as claimed in claim 1, further comprising:

the variable pressure assembly comprising a motor, a cam, a piston and a hollow cylinder;

the hollow cylinder comprising a first end and a second end;

the cam being axially mounted to a drive-shaft of the motor;

the cam being perimetrically pressed against the piston;

the piston slidably and sealably engaging the hollow cylinder;

the piston traversing through the first end of the hollow cylinder; and the second end of the hollow cylinder being in fluid communication with the inner catheter tube.

* * * * *